(12) United States Patent
Park et al.

(10) Patent No.: US 10,398,535 B2
(45) Date of Patent: Sep. 3, 2019

(54) INDICATOR FOR IMPROVING SCANNING PRECISION, COMPOSITION FOR IMPROVING SCANNING PRECISION, AND METHOD FOR IMPROVING SCANNING PRECISION OF ARTICLE

(71) Applicants: Sung Won Park, Gyeonggi-do (KR); June Beom Park, Incheon (KR)

(72) Inventors: Sung Won Park, Gyeonggi-do (KR); June Beom Park, Incheon (KR)

( * ) Notice: Subject to any disclaimer, the term of this patent is extended or adjusted under 35 U.S.C. 154(b) by 0 days.

(21) Appl. No.: 16/078,747

(22) PCT Filed: Nov. 29, 2016

(86) PCT No.: PCT/KR2016/013871
§ 371 (c)(1),
(2) Date: Aug. 22, 2018

(87) PCT Pub. No.: WO2017/146351
PCT Pub. Date: Aug. 31, 2017

(65) Prior Publication Data
US 2019/0046303 A1    Feb. 14, 2019

(30) Foreign Application Priority Data
Feb. 22, 2016 (KR) .................. 10-2016-0020691

(51) Int. Cl.
| | |
|---|---|
| *G06T 7/00* | (2017.01) |
| *A61C 9/00* | (2006.01) |
| *A61C 19/04* | (2006.01) |
| *A61B 90/00* | (2016.01) |
| *A61B 5/00* | (2006.01) |
| *G06F 19/00* | (2018.01) |

(Continued)

(52) U.S. Cl.
CPC .......... *A61C 9/0053* (2013.01); *A61B 5/0062* (2013.01); *A61B 5/0088* (2013.01); *A61B 5/4547* (2013.01); *A61B 90/00* (2016.02); *A61C 13/34* (2013.01); *A61C 19/04* (2013.01); *A61K 6/002* (2013.01); *G06F 19/00* (2013.01); *G06T 7/0014* (2013.01); *A61B 5/055* (2013.01); *A61B 2090/363* (2016.02)

(58) Field of Classification Search
None
See application file for complete search history.

(56) References Cited

U.S. PATENT DOCUMENTS

| | | | |
|---|---|---|---|
| 2006/0154198 A1* | 7/2006 | Durbin | ................. A61C 9/00 433/29 |
| 2008/0180436 A1 | 7/2008 | Kraver | |

(Continued)

FOREIGN PATENT DOCUMENTS

| | | |
|---|---|---|
| KR | 10-1256194 B1 | 4/2013 |
| KR | 10-1332335 B1 | 11/2013 |

(Continued)

*Primary Examiner* — Delomia L Gilliard
(74) *Attorney, Agent, or Firm* — Harrington & Smith

(57) ABSTRACT

Provided is an indicator for enhancing scanning precision, a composition for enhancing scanning precision, and a method of enhancing scanning precision of an article. The disclosed indicator serves to adjust, to an absolute size, a relative size of each of a plurality of images acquired by scanning a subject with a scanner, and to align each image according to position.

20 Claims, 3 Drawing Sheets

(51) Int. Cl.
    *A61C 13/34*    (2006.01)
    *A61K 6/00*     (2006.01)
    *A61B 5/055*    (2006.01)

(56) References Cited

U.S. PATENT DOCUMENTS

| | | |
|---|---|---|
| 2010/0030083 A1 | 2/2010 | Sanders et al. |
| 2010/0198566 A1 | 8/2010 | Lauren .............................. 703/1 |
| 2013/0244199 A1* | 9/2013 | Lu ............................ C09D 7/61 |
| | | 433/82 |
| 2015/0209118 A1* | 7/2015 | Kopelman ........... A61C 9/0053 |
| | | 433/25 |
| 2015/0348320 A1 | 12/2015 | Pesach et al. |
| 2016/0367336 A1* | 12/2016 | Lv ......................... A61C 1/0046 |
| 2017/0202483 A1* | 7/2017 | Sorimoto ............. A61B 5/0088 |

FOREIGN PATENT DOCUMENTS

| | | |
|---|---|---|
| KR | 10-2017-0007064 A | 1/2017 |
| WO | WO-2011/112454 A1 | 9/2011 |
| WO | WO-2013/173142 A1 | 11/2013 |

\* cited by examiner

INDICATOR FOR IMPROVING SCANNING PRECISION, COMPOSITION FOR IMPROVING SCANNING PRECISION, AND METHOD FOR IMPROVING SCANNING PRECISION OF ARTICLE

This patent application is a U.S. National Stage application of International Patent Application Number PCT/KR2016/013871 filed Nov. 29, 2016, and claims priority to KR 10-2016-0020691 filed Feb. 22, 2016 which are hereby incorporated by reference in their entireties.

TECHNICAL FIELD

The present disclosure relates to an indicator for enhancing scanning precision, a composition for enhancing scanning precision, and a method of enhancing scanning precision of an article. More particularly, the present disclosure relates to an indicator for enhancing scanning precision, which serves to adjust, to an absolute size, a relative size of each of a plurality of images acquired by scanning a subject with a scanner, and align the each image according to position, a composition for enhancing scanning precision, which includes the indicator for enhancing scanning precision, and a method of enhancing scanning precision of an article by using the composition.

BACKGROUND ART

Recently, in dental hospitals and the like, a method of directly acquiring three-dimensional shape data (i.e., an image) inside the oral cavity of a patient by using a scanner, and then processing a prosthesis, which is applied to the oral cavity of the human body, by using the acquired three-dimensional shape data has been used. This method is referred to a method of processing a prosthesis by using computer aided design (CAD)/computer aided manufacturing (CAM).

However, a very large size of scanner is required to acquire three-dimensional shape data in the entirety of the oral cavity of a patient at once, and in this case, it is difficult to actually insert such a big scanner into the oral cavity, and even if such a big scanner can be inserted into the oral cavity, it causes a patient to feel much inconvenience. Thus, three-dimensional shape data is generally acquired by inserting a scanner with a small size into the oral cavity and three-dimensionally scanning an internal structure of the oral cavity while continually changing a position of the scanner to acquire a plurality of scanning data according to position, and then composing (i.e., combining) these data. However, when the internal structure of the oral cavity is scanned with a scanner, a distance and angle between the scanner and a subject are continually changed, and thus in CAD, respective images are compared with each other and combined according to a combining scheme based on a relative coordinate system to form a three-dimensional structure, but the formed three-dimensional structure is considerably different from the actual subject. That is, for composing or combining scanning data for respective positions, it is necessary to adjust, to a predetermined size, a size of each of images realized by the scanning data, and then directly connect a scanning datum for any one of the positions to a scanning datum for a position adjacent thereto. However, conventionally, such a composing or combining method is virtually impossible, and thus finally acquired three-dimensional shape data is not substantially inconsistent with an actual internal structure of the oral cavity. Therefore, a prosthesis manufactured by using the three-dimensional shape data also has a different shape from that of an actual internal structure of the oral cavity, resulting in dental aftereffects such as malocclusion, tooth deformation, or a headache.

DESCRIPTION OF EMBODIMENTS

Technical Problem

Provided is an indicator for enhancing scanning precision, which serves to adjust, to an absolute size, a relative size of each of a plurality of images acquired by scanning a subject with a scanner, and then align each image according to position.

Provided is a composition for enhancing scanning precision, which includes the above-described indicator for enhancing scanning precision.

Provided is a method of enhancing scanning precision of an article.

Solution to Problem

According to an aspect of the present disclosure, there is provided an indicator for enhancing scanning precision, the indicator being configured to adjust, to an absolute size, a relative size of each of a plurality of images, wherein the plurality of images being acquired by scanning a subject with a scanner, and to align each image according to position.

The indicator may include a metal, an alloy, a non-metal, or a combination thereof.

The indicator may have a three-dimensional structure, a planar structure, or a combination thereof.

The indicator may have a circular, oval, rectangular, square, pentagonal, or hexagonal cross-sectional shape.

The indicator may have an average size of 1 µm to 1,000 µm.

According to another aspect of the present disclosure, there is provided a composition for enhancing scanning precision, the composition including the above-described indicator and a light scannability enhancer.

The light scannability enhancer may further include a white pigment, a binder resin, and a solvent for dissolving the binder resin.

Amounts of the binder resin and the solvent may be in a range of 12 parts by weight to 30 parts by weight and in a range of 50 parts by weight to 700 parts by weight, respectively, with respect to 100 parts by weight of the white pigment.

The white pigment may have an average particle diameter of 50 nm to 400 nm.

The white pigment may include at least one selected from the group consisting of titanium dioxide, zinc oxide, zinc sulfide, lithopone, lead white, and antimony oxide.

The binder resin may include a natural resin, a synthetic resin, rubber, or a mixture of two or more thereof.

The solvent may include a volatile material.

The solvent may include at least one of water and an alcohol.

The light scannability enhancer may have a viscosity of 3 cps to 120 cps.

The light scannability enhancer may further include a dispersant in an amount of 0.5 parts by weight to 10 parts by weight with respect to 100 parts by weight of the white pigment.

At least one of the white pigment, the binder resin, the solvent, and the dispersant may be approved by the US Food and Drug Administration (FDA).

According to another aspect of the present disclosure, there is provided a method of enhancing scanning precision of an article, the method including applying the above-described indicator or the above-described composition to an article.

The method may further include removing the solvent from the article to which the composition is applied.

The article may be a metal or a non-metal.

The article may be a tooth or a tooth model.

The article may be a natural tooth in the oral cavity, an implant abutment in the oral cavity, or a gingiva.

Advantageous Effects of Disclosure

A composition for enhancing scanning precision, according to an embodiment of the present disclosure, includes an indicator. Thus, when the composition for enhancing scanning precision is applied to the oral cavity of a patient, and then three-dimensional shape data of the oral cavity is directly acquired using a scanner, three-dimensional shape data that almost perfectly reproduces an actual internal structure of the oral cavity may be acquired. Accordingly, a prosthesis manufactured using the three-dimensional shape data also has almost the same shape as that of an actual internal structure of the oral cavity, and thus dental aftereffects such as malocclusion, tooth deformation, or a headache do not occur.

In addition, when the composition for enhancing scanning precision is used, a coating film having a uniform thickness is repeatedly and reproducibly formed on a surface of a tooth, the gingiva, or a tooth model, and thus it is possible to obtain accurate and reproducible scanning data. In addition, the composition for enhancing scanning precision can be directly applied to an article and is not harmful to the human body. In addition, the composition for enhancing scanning precision may also be applied to a non-metal article such as glass or plaster, as well as a metal article.

In addition, a coating film prepared from the composition for enhancing scanning precision is not easily dissolved in saliva, and thus may have high shape retention even in the oral cavity and may also be easily separated from an article after optical scanning.

In addition, a method of enhancing scanning precision of an article, according to an embodiment of the present disclosure, is advantageous in that a manufacturing process is simple and processing cost is low, compared to a conventional method such as application using a paste or fusion of titanium powder by high-temperature sintering.

MODE OF DISCLOSURE

Figure 1:
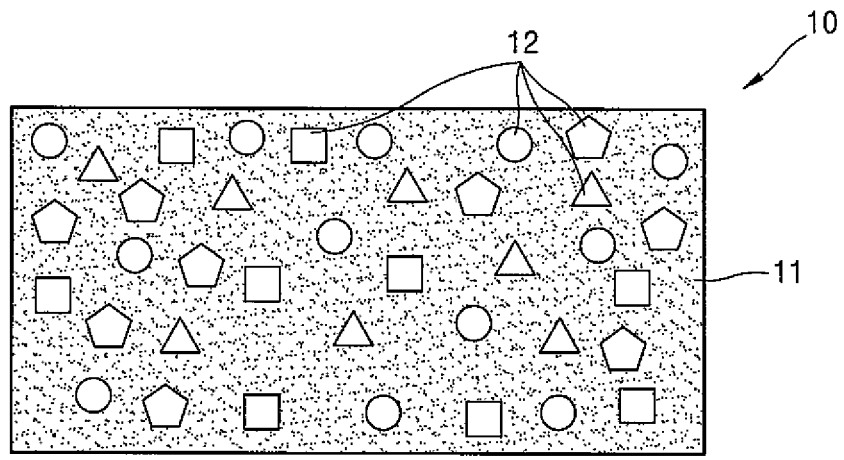
FIG. 1 is a view of a composition for enhancing scanning precision, according to an embodiment of the present disclosure.

Hereinafter, an indicator for enhancing scanning precision, according to an embodiment of the present disclosure, will be described in detail.

An indicator for enhancing scanning precision (hereinafter, also simply referred to as an indicator), according to an embodiment of the present disclosure, may be attached or applied to an article. Examples of a method of attaching the indicator to an article include a method of attaching the indicator to an article using a tape and a method of sprinkling the indicator in a powder form onto an article, but the present disclosure is not particularly limited thereto. Examples of a method of applying the indicator to an article includes a method of adding the indicator to a liquid composition and applying the resulting composition to an article and a method of adding the indicator to a paste and applying the resulting paste to an article, but the present disclosure is not particularly limited thereto.

When an article (i.e., a subject) to which the indicator for enhancing scanning precision is attached is scanned with a scanner, the indicator for enhancing scanning precision may be scanned along with the article and included in scanning data.

The indicator for enhancing scanning precision serves to adjust, to an absolute size, a relative size of each of a plurality of images acquired by scanning a subject with a scanner, and then align each image according to position. As used herein, the term "relative size" refers to a size of images on which a deviation due to a difference in scanning position and scanning angle exists, and the term "absolute size" refers to a size of images from which a deviation due to a difference in scanning position and scanning angle is removed or reduced.

In particular, the indicator for enhancing scanning precision, which refers to a fine particle with a predetermined size, may correct distortion of scanned images when the indicator is attached or applied to a subject and the subject is scanned with a scanner, and, when composing the images, may easily find accurate combination points and align each image according to position. That is, a relative size of each image is adjusted to an absolute size by enlarging or reducing a size of the indicator included in each image to a predetermined size of indicator, and then automatically perform puzzle alignment in a CAD program to obtain indicators having complete shapes by comparing the shapes of the indicators included in the images to each other, thereby aligning each image according to position. As a result, an image of a three-dimensional structure, which has exactly the same or almost the same structure as that of an actual subject, may be acquired in CAD, and accordingly, a three-dimensional structure having exactly the same or almost the same structure as that of an actual subject may be processed by CAM.

The indicator for enhancing scanning precision may include a metal, an alloy, a non-metal, or a combination thereof. A material of the indicator for enhancing scanning precision is not particularly limited.

The indicator for enhancing scanning precision may have a three-dimensional structure, a planar structure, or a combination thereof.

The indicator for enhancing scanning precision may have a circular, oval, rectangular, square, pentagonal, or hexagonal cross-sectional shape. However, the present disclosure is not limited to the above examples, and the indicator for enhancing scanning precision may have various other cross-sectional shapes.

The indicator for enhancing scanning precision may have various colors. For example, the indicator for enhancing scanning precision may have a white color, a black color, a red color, a brown color, or a gray color.

The indicator for enhancing scanning precision may include a plurality of indicators for enhancing scanning precision. The plurality of indicators may include indicators having only one cross-sectional shape. In some embodiments, the plurality of indicators may include two or more indicators having different cross-sectional shapes. For example, the plurality of indicators may include at least one selected from an indicator having a circular cross-sectional shape, an indicator having an oval cross-sectional shape, an indicator having a rectangular cross-sectional shape, an indicator having a square cross-sectional shape, an indicator having a pentagonal cross-sectional shape, and an indicator having a hexagonal cross-sectional shape.

As the type of indicator included in the plurality of indicators varies, a scanning precision enhancement effect of the indicator for enhancing scanning precision is increased.

The indicator for enhancing scanning precision may have an average size of 1 μm to 1,000 μm, for example, 10 μm to 500 μm. However, the present disclosure is not limited to the above examples, and the indicator for enhancing scanning precision may have various other sizes.

A composition for enhancing scanning precision, according to an embodiment of the present disclosure, includes the above-described indicator for enhancing scanning precision and a light scannability enhancer.

When an article to which the composition for enhancing scanning precision is applied is scanned with a scanner, the indicator for enhancing scanning precision is scanned along with the article and included in scanning data (i.e., an image realized by CAD). In particular, a plurality of scanning data according to position is acquired by inserting, into the oral cavity, a scanner having a smaller size than that of the oral cavity and three-dimensionally scanning an internal structure of the oral cavity while continually changing a position of the scanner. Subsequently, a scanning datum for any one of the plurality of positions is directly connected to a scanning datum for a position adjacent thereto using data of the indicator for enhancing scanning precision, among the plurality of scanning data according to position, and the plurality of scanning data according to position are composed or combined by adjusting the size of each image, thereby acquiring three-dimensional shape data. That is, the indicator for enhancing scanning precision align the plurality of scanning data according to position to correspond to a position of the article, and serves to adjust, to an absolute size, a size of each of images obtained by the plurality of scanning data according to position. Accordingly, a structure of the article may be almost perfectly reproduced as the three-dimensional shape data in CAD, and a prosthesis produced by CAM using the three-dimensional shape data may have almost the same shape as that of the article.

The indicator for enhancing scanning precision may not be dissolved in a solvent included in the light scannability enhancer. Thus, the indicator for enhancing scanning precision may be maintained in a solid state in the composition for enhancing scanning precision.

The light scannability enhancer includes a white pigment, a binder resin, and a solvent for dissolving the binder resin.

Amounts of the binder resin and the solvent may be in a range of 12 parts by weight to 30 parts by weight and in a range of 50 parts by weight to 700 parts by weight, respectively, with respect to 100 parts by weight of the white pigment.

When the amount of the binder resin is within the above range, a coating film formed from the composition for enhancing scanning precision is not dissolved in moisture (e.g., saliva), and thus light scanning characteristics of an article are not deteriorated and the coating film is easily separated from the article even after optical scanning, and the coating film formed from the composition for enhancing scanning precision has a uniform thickness at any position so that light scanning characteristics of an article are maintained at a high level.

When the amount of the solvent is within the above range, the relative amount of the white pigment is appropriate, and thus it is possible to uniformly distribute the white pigment on an article by coating the composition for enhancing scanning precision on the article, and when forming a coating film, the white pigment has excellent hiding power.

The white pigment serves to induce diffuse reflection during optical scanning of an article and allows the article to exhibit a white color (i.e., a color similar to that of a tooth).

The white pigment may have an average particle diameter of 50 nm to 400 nm (e.g., 100 nm to 300 nm). When the average particle diameter of the white pigment is within the above range (50 nm to 400 nm), it is advantageous for shape recognition due to high hiding power of the white pigment, and an excellent diffuse reflection effect may also be obtained.

The white pigment may include at least one selected from the group consisting of titanium dioxide ($TiO_2$), zinc oxide, zinc sulfide, lithopone, lead white, and antimony oxide.

The binder resin may include a natural resin, a synthetic resin, rubber, or a mixture of two or more thereof. In particular, the binder resin may be a thermoplastic resin or a thermosetting resin. More particularly, the binder resin may include at least one selected from the group consisting of poly(lactic-co-glycolic acid) (PLGA); rosin; shellac; vinyl chloride resin; vinyl acetate resin; a vinyl chloride/vinyl acetate copolymer (e.g., UCAR™ VYHH); a vinyl chloride/vinyl acetate/vinyl alcohol copolymer (e.g., UCAR™ VAGH); alkyd resin; polyester-based resins such as polyglycolic acid, polylactic acid, polycaprolactone, polyethylene adipate, polyhydroxyalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, and vectran; polyurethane-based resins such as spandex; epoxy-based resins such as bisphenol A type epoxy resin, bisphenol F type epoxy resin, resorcinol type epoxy resin, phenol novolac type epoxy resin, and cresol novolac type epoxy resin; and acryl-based resins such as polymethylacrylate and polymethylmethacrylate.

The solvent not only serves to dissolve the binder resin, but also enhances spreadability of the composition for enhancing scanning precision when the composition is applied to an article, so that the composition is applied to the article with a uniform thickness.

The solvent may include a volatile material. Accordingly, the solvent may be naturally evaporated from an article to which the composition for enhancing scanning precision is applied, within a short time period. That is, the composition for enhancing scanning precision that is applied to the article may be naturally dried within a short time period since the solvent is rapidly evaporated.

The solvent may include at least one of water and an alcohol. In particular, the solvent may include ethanol. However, the present disclosure is not limited to the above example, and the solvent may include any organic solvent and/or an inorganic solvent that are/is more volatile than water.

The light scannability enhancer may have a viscosity of 3 centipoises (cps) to 120 cps. When the viscosity of the light scannability enhancer is within the above range, a coating film with a uniform and appropriate thickness may be formed. As used herein, the term "viscosity" refers to a viscosity measured at room temperature (25° C.) using DV-III Rheometer RPM (shear rate: 25/s) manufactured by Brookfield.

The light scannability enhancer may further include a dispersant in an amount of 0.5 parts by weight to 10 parts by weight with respect to 100 parts by weight of the white pigment.

When the amount of the dispersant is within the above range, agglomeration of the white pigment may be prevented without a substantial increase in manufacturing cost, and a coating film having excellent diffusereflection effect may be formed.

The dispersant serves to enhance inter-particle density of the white pigment in a coating film formed by applying the composition for enhancing scanning precision to an article and increase adhesion between the coating film and the article.

The dispersant may be a surfactant. In particular, the dispersant may include: a non-ionic surfactant (e.g., polyvinyl alcohol, polyacrylic acid, polyoxyethylene lauryl ether, and sodium lauryl sulfate); a cationic surfactant (e.g., $C_{12}$-$C_{16}$ alkyl benzene dimethyl ammonium chloride, $C_8$-$C_{18}$ alkyl trimethyl ammonium chloride, or distearyl dimethyl ammonium chloride); an anionic surfactant (e.g., sodium dodecyl sulfate or sodium dodecylbenzene sulfonate); a zwitterionic surfactant (e.g., an amino acid-type surfactant, a myristyl betaine-type surfactant, a glycine-type surfactant, an alanine-type surfactant, a sulfobetaine-type surfactant, lecithin, or taurine); or a combination thereof.

At least one of the white pigment, the binder resin, the solvent, and the dispersant may be approved by the US Food and Drug Administration (FDA).

The light scannability enhancer may be a suspension in which titanium dioxide is dispersed in a liquid material (the suspension is also referred to as a liquid composition for enhancing scanning precision). The liquid material may include the solvent, a binder resin dissolved in the solvent, and optionally, a dispersant dissolved in the solvent.

FIG. 1 is a view of a composition 10 for enhancing scanning precision, according to an embodiment of the present disclosure.

Referring to FIG. 1, the composition 10 for enhancing scanning precision includes a light scannability enhancer 11 and an indicator 12 for enhancing scanning precision.

Hereinafter, a method of enhancing scanning precision of an article, according to an embodiment of the present disclosure, will be described in detail with reference to FIG. 2.

Figure 2:
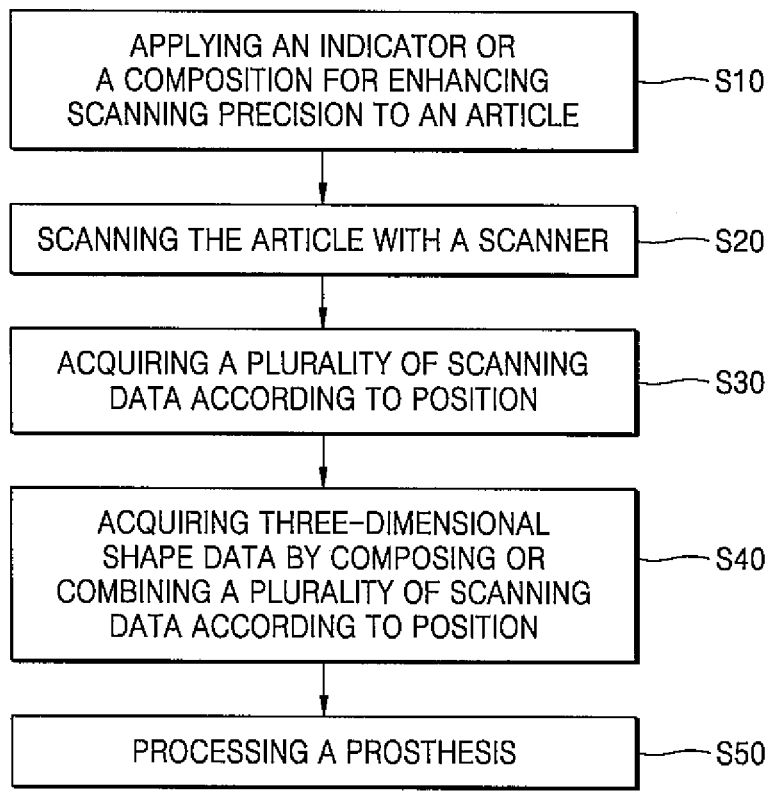
FIG. 2 is a flowchart illustrating a method of enhancing scanning precision of an article, according to an embodiment of the present disclosure.

FIG. 2 is a flowchart illustrating a method of enhancing precision of scanning of an article, according to an embodiment of the present disclosure.

Referring to FIG. 2, the method of enhancing precision of scanning of an article includes attaching or applying an indicator for enhancing scanning precision to an article, or applying a composition for enhancing scanning precision to an article (operation S10), scanning the article with a scanner (operation S20), acquiring a plurality of scanning data according to position (operation S30), acquiring three-dimensional shape data by composing or combining the plurality of scanning data according to position (operation S40), and optionally, processing a prosthesis by using the three-dimensional shape data (operation S50).

The applying (operation S10) may be performed using a sprayer or a brush. For example, the applying (operation S10) may be performed by wetting a brush with the composition and brushing the article with the wet brush. For example, the brushing may be performed once.

The method may further include removing the solvent from the article to which the composition for enhancing scanning precision is applied (not shown). The removing of the solvent may be performed by natural drying. However, the removing of the solvent may be omitted when an indicator for enhancing scanning precision is used in the applying process (operation S10).

The article may be a metal or a non-metal.

The metal may be, but is not limited to, titanium, iron, tin, zinc, copper, or an alloy thereof.

The non-metal may be, but is not limited to, glass, plaster, wax, plastic, a tooth or gingiva in the oral cavity, an implant abutment in the oral cavity, or a cellular phone case.

The article may be a tooth or a tooth model. However, the present disclosure is not limited thereto, and the article may be any article capable of being optically scanned.

Hereinafter, the scanning process (operation S20) and the acquiring of the scanning data (operation S30) will be described in detail with reference to FIG. 3.

Figure 3:
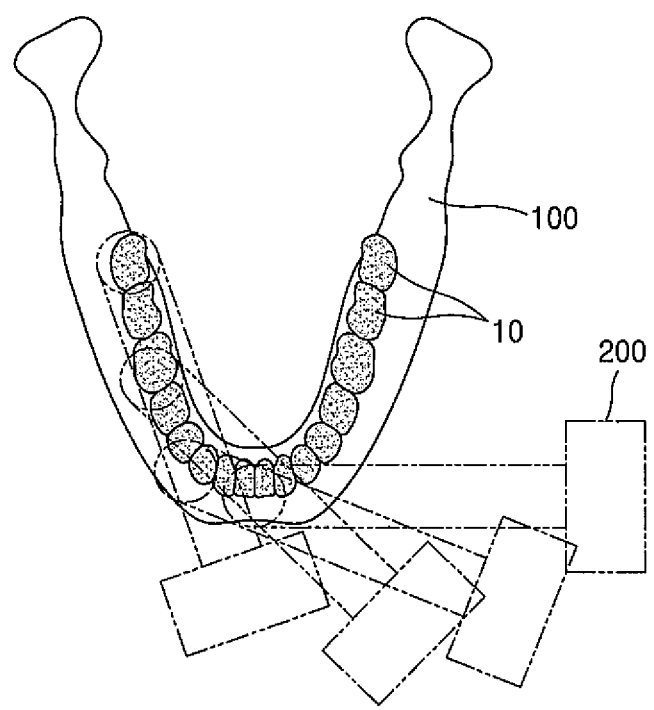
FIG. 3 is a view illustrating a process of scanning teeth, to which a composition for enhancing scanning precision, according to an embodiment of the present disclosure, is applied, with a scanner.

FIG. 3 is a view illustrating a process of scanning, with a scanner 200, a tooth 100 to which a composition 10 for enhancing scanning precision, according to an embodiment of the present disclosure, is applied.

Referring to FIG. 3, the scanner 200 is inserted into the oral cavity and the tooth 100 to which the composition 10 for enhancing scanning precision is applied is three-dimensionally scanned while continually changing a position of the scanner 200, thereby acquiring a plurality of scanning data according to position (not shown).

Hereinafter, the acquiring of the three-dimensional shape data (operation S40) will be described in detail with reference to FIG. 4.

Figure 4:
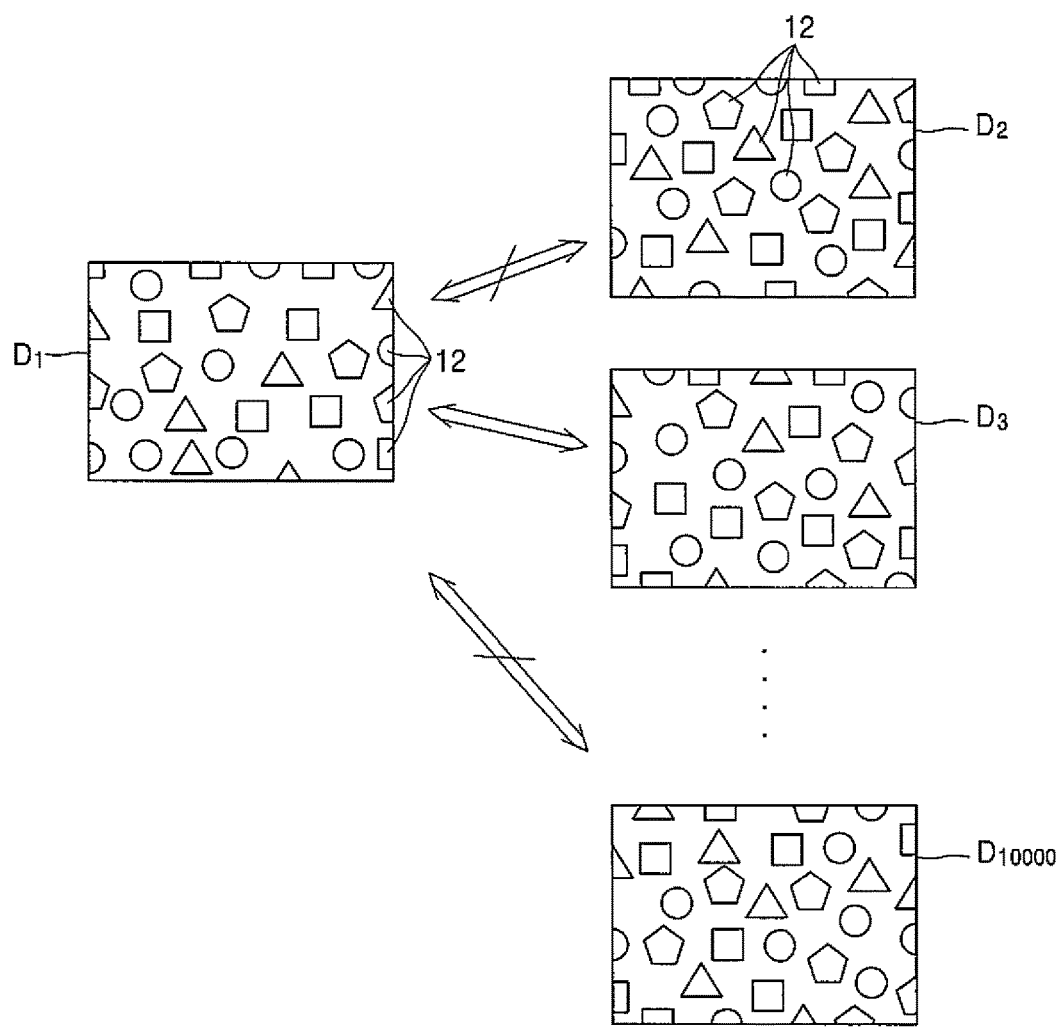
FIG. 4 is a view for explaining a principle of composing or combining a plurality of scanning data according to position by using an indicator.

FIG. 4 is a view for explaining a principle of composing or combining a plurality of scanning data according to position D1, D2, D3, . . . , and D10000 by using indicators 12.

Referring to FIG. 4, a size of an image realized by the scanning data for each position D1, D2, D3, . . . , or D10000 is adjusted to a predetermined size using data of the indicators 12 among the scanning datum for each position D1, D2, 03, . . . , or D10000, and the plurality of scanning data according to position D1, D2, D3, . . . , and D10000 are composed or combined together by directly connecting the scanning datum D1 for any one of the plurality of positions to the scanning datum D3 for a position adjacent thereto, thereby acquiring three-dimensional shape data. In particular, referring to FIG. 4, a part of an indicator 12 having a triangular cross-sectional shape, a part of an indicator 12 having a circular cross-sectional shape, a part of an indicator 12 having a pentagonal cross-sectional shape, and a part of an indicator 12 having a tetragonal cross-sectional shape are present at an edge on the right side of the scanning datum D1, and when adjusting a size of each indicator 12 to a predetermined size, among the other scanning data for each position D2, D3, . . . , and D10000 except for the scanning datum D1, data to be combined to the parts of the indicators 12 included in the scanning datum D1 so as to form the indicator 12 having a complete triangular cross-sectional shape, the indicator 12 having a complete circular cross-sectional shape, the indicator 12 having a complete pentagonal cross-sectional shape, and the indicator 12 having a complete tetragonal cross-sectional shape is only the scanning datum D3 having, at an edge on the left side thereof, a part of the indicator 12 having a triangular cross-sectional shape, a part of the indicator 12 having a circular cross-sectional shape, a part of the indicator 12 having a pentagonal cross-sectional shape, and a part of the indicator 12 having a tetragonal cross-sectional shape. Thus, the scanning datum D3 is directly connected to the scanning datum D1. The other scanning data D2, D4, ..., and D10000 are also consecutively connected to the scanning datum D1 or the scanning datum D3 in the same manner as described above. Three-dimensional shape data acquired in this manner may almost perfectly reproduce a structure of the tooth 100, and a prosthesis (not shown) produced using the three-dimensional shape data may have almost the same shape as that of the tooth 100.

In addition, the method is directly applicable to an article, and when the method is used, a manufacturing process may be simple and device cost and processing cost may be reduced, as compared to an existing method of applying a paste using a coating apparatus or an existing method of fusing titanium powder by high-temperature sintering, and a coating film with a uniform thickness may be reproducibly obtained on a plurality of articles. As such, when a coating film with a uniform thickness can be reproducibly obtained on a plurality of articles, accurate scanning data may be reproducibly acquired.

Preparation examples and evaluation examples of the light scannability enhancer (i.e., a portion except for the indicator) included in the composition for enhancing scanning precision, according to an embodiment of the present disclosure, are disclosed in Korean Patent Application No. 2015-0119838. The disclosure of Korean Patent Application No. 2015-0119838 is incorporated herein in its entirety by reference.

Although example embodiments of the present disclosure have been described with reference to the accompanying drawings and examples, these embodiments are provided only for illustrative purposes, and it will be understood by one of ordinary skill in the art to which the present disclosure pertains that various modifications and other embodiments equivalent thereto can be made. Thus, the scope of the present disclosure should be defined by the appended claims.

The invention claimed is:

1. A method of enhancing precision of scanning of an article, the method comprising:
   attaching or applying, to an article, an indicator for enhancing scanning precision, or applying, to an article, a composition for enhancing scanning precision, the composition comprising the indicator;
   scanning the article with a scanner;
   acquiring a plurality of scanning data according to position; and
   acquiring three-dimensional shape data by composing or combining the acquired plurality of scanning data,
   wherein the indicator is configured to adjust, to an absolute size, a relative size of each of a plurality of images, the plurality of images being acquired by scanning the article with the scanner, and to align each image according to position, and
   in the acquiring of the three-dimensional shape data, the three-dimensional shape data is acquired by adjusting, to a predetermined size, a size of each of images realized by the plurality of scanning data according to position, by using data of the indicators among the plurality of scanning data according to position acquired in the acquiring of the scanning data, and composing or combining the plurality of scanning data according to position together such that scanning datum for any one of the plurality of positions is directly connected to scanning datum for a position adjacent thereto.

2. The method of claim 1, further comprising processing a prosthesis using the three-dimensional shape data, the three-dimensional shape data being acquired in the acquiring of the three-dimensional shape data.

3. The method of claim 1, wherein the attaching or applying is performed using a sprayer or a brush.

4. The method of claim 1, wherein, when the applying is performed using a composition for enhancing scanning precision, the method further comprises, between the applying and the scanning, removing a solvent from the article to which the composition is applied.

5. The method of claim 1, wherein the indicator comprises a metal, an alloy, a non-metal, or a combination thereof.

6. The method of claim 1, wherein the indicator has a three-dimensional structure, a planar structure, or a combination thereof.

7. The method of claim 1, wherein the indicator has a circular, oval, rectangular, square, pentagonal, or hexagonal cross-sectional shape.

8. The method of claim 1, wherein the indicator has an average size of 1 μm to 1,000 μm.

9. The method of claim 1, wherein the composition further comprises a light scannability enhancer.

10. The method of claim 9, wherein the light scannability enhancer comprises a white pigment, a binder resin, and a solvent for dissolving the binder resin.

11. The method of claim 10, wherein amounts of the binder resin and the solvent are in a range of 12 parts by weight to 30 parts by weight and in a range of 50 parts by weight to 700 parts by weight, respectively, with respect to 100 parts by weight of the white pigment.

12. The method of claim 10, wherein the white pigment has an average particle diameter of 50 nm to 400 nm.

13. The method of claim 10, wherein the white pigment comprises at least one selected from the group consisting of titanium dioxide, zinc oxide, zinc sulfide, lithopone, lead white, and antimony oxide.

14. The method of claim 10, wherein the binder resin comprises a natural resin, a synthetic resin, rubber, or a mixture of two or more thereof.

15. The method of claim 10, wherein the solvent comprises a volatile material.

16. The method of claim 15, wherein the solvent comprises at least one of water and an alcohol.

17. The method of claim 9, wherein the light scannability enhancer has a viscosity of 3 cps to 120 cps.

18. The method of claim 10, wherein the light scannability enhancer further comprises a dispersant in an amount of 0.5 parts by weight to 10 parts by weight with respect to 100 parts by weight of the white pigment.

19. The method of claim 1, wherein the article is a metal or a non-metal.

20. The method of claim 19, wherein the article is a tooth or a tooth model.

* * * * *